US007377279B1

(12) United States Patent
Malaspina

(10) Patent No.: US 7,377,279 B1
(45) Date of Patent: May 27, 2008

(54) PORTABLE RESUSCITATION ORGANIZER PLATFORM

(76) Inventor: Paul J. Malaspina, 5111 Ellington Dr., Erie, PA (US) 16506

(*) Notice: Subject to any disclaimer, the term of this patent is extended or adjusted under 35 U.S.C. 154(b) by 342 days.

(21) Appl. No.: 11/125,621

(22) Filed: May 9, 2005

(51) Int. Cl.
*A61F 5/37* (2006.01)
*A47B 7/00* (2006.01)

(52) U.S. Cl. .......................... 128/870; 5/621; 206/570

(58) Field of Classification Search ........ 206/570–572, 206/370, 803; 5/600, 620–622, 628, 658, 5/503.1, 419, 420, 625–627; 128/870; 383/4, 383/6, 38–40
See application file for complete search history.

(56) References Cited

U.S. PATENT DOCUMENTS 4,513,866 A * 4/1985 Thomas ...................... 206/570
4,984,906 A * 1/1991 Little ............................ 383/4
5,056,533 A * 10/1991 Solano .......................... 5/627
5,094,418 A * 3/1992 McBarnes et al. ............. 5/658
5,581,829 A * 12/1996 Lee ............................ 383/39
5,622,300 A * 4/1997 Robinson ....................... 383/4
5,720,303 A * 2/1998 Richardson .................... 5/627
5,749,374 A * 5/1998 Schneider, Sr. ............. 128/870
6,061,849 A * 5/2000 Seals ............................. 5/417
6,334,519 B1* 1/2002 Tong .......................... 190/107
6,848,132 B1* 2/2005 Dale ........................... 383/38
6,912,747 B2* 7/2005 DuPree et al. ................. 5/625
2002/0083525 A1* 7/2002 Zheng ........................... 5/420

* cited by examiner

*Primary Examiner*—Luan K Bui
(74) *Attorney, Agent, or Firm*—Richard K Thomson

(57) ABSTRACT

A patient support platform contains medical supplies which are anatomically arranged about the supported patient. The supply compartments and envelopes have see-through closures with pull tabs to make easy identification and access of the items possible. Resilient backing members push the items in the compartments to the front where they are readily accessible. A collapsible IV support pole is stored within the platform and a plurality of apertures provide support locations for the pole. The platform can be rolled up like a bedroll and stored in a satchel for storage and transport.

20 Claims, 4 Drawing Sheets

PORTABLE RESUSCITATION ORGANIZER PLATFORM

BACKGROUND AND SUMMARY OF THE INVENTION

The present invention is directed to the field of medical care. More particularly, the present invention is directed to a portable resuscitation organizer platform which can be used in a medical emergency.

In most medical emergencies, time is of the essence. A matter of one minute can make the difference between resuscitating a victim to complete health and losing them to a persistent vegetative state or, perhaps, being unable to revive them at all. Within hospitals, equipment stored in cabinets and on shelves and in "crash carts" are used to handle emergencies requiring Cardio-Pulmonary Resuscitation (CPR) and a variety of invasive medical procedures constituting advanced life support. The "crash carts" are typically quite bulky and frequently left outside the immediate vicinity of the patient, necessitating calling out for items which are retrieved by others and passed in, or running back and forth to obtain and apply the necessary medical equipment. These carts are entirely unsuitable for dealing with medical emergencies outside of the hospital setting such as at the scene of a vehicle crash or in an ambulance as the patient is transported to the hospital. In the pre-hospital setting, equipment and supplies are stuffed into packs and kits stored in compartments in the interior or exterior of the vehicle. The difficulties of initiating Emergency Medical Service (EMS) resuscitations in the field are compounded by weather conditions, poor lighting, vehicle motion and lack of assistance.

Various attempts have been made to store medical equipment in transportable devices to enable paramedics to revive victims at accident scenes or in transport vehicles. For example, U.S. Pat. No. 3,986,505 to Power stores supplies for emergency burn treatment and U.S. Pat. No. 4,513,866 to Thomas discloses a medical satchel with pockets for storing supplies for medical emergencies. Other similar devices include U.S. Pat. No. 5,931,303 to Salvadori which provides a storage roll for sterile medical equipment for such procedures as urethral catheterization. These prior art devices suffer from a number of deficiencies. They are little more than glorified knapsacks; while they do provide space for storage, they do not put the needed supplies at the caregiver's fingertips, in the immediate vicinity of the patient, or at the immediate anatomical site of use. Searching for the right medical equipment results in critical time delays which jeopardize the survival of the patient. Further, these devices are not intended to support the victim during the procedure. An ambulance stretcher, gurney or hospital bed has a cushion or mattress which renders cardiac compressions during CPR ineffective. Thus, a piece of plywood, or similar board, is typically placed under the patient before beginning CPR.

These shortcomings of the prior art are overcome by the portable resuscitation organizer platform (P.R.O.P.) of the present invention. The platform is designed to underlie the patient and the necessary medical equipment is anatomically arranged around the patient in regions adjacent specific body portions where items contained in the compartments will be needed for procedures performed on the patient. The patient support zone has a recessed portion for receiving and retaining the patient's head. This region may have additional padding for the patient's comfort. The storage compartments are provided with see-through closures to enable the contents to be quickly determined without the need for opening the compartments. Some of the compartments are provided with a resilient backing means to push the contents to the front of the compartment where they may be quickly accessed. The platform can be collapsed for easy transport to the location of the emergency, where it is unrolled, and the patient placed upon it. The platform can be stored in an enclosing carrier bag for extended periods of storage between uses. The carrier bag also facilitates transport to and from the location of the emergency. The P.R.O. platform is provided with a collapsible intravenous (IV) support stand and a plurality of receptacles which can receive it during use.

Various other features, advantages and characteristics of the present invention will become apparent to one of ordinary skill in the art after a reading of the following specification.

BRIEF DESCRIPTION OF THE DRAWINGS

The preferred embodiment(s) of the present invention is/are described in conjunction with the associated drawings in which like features are indicated with like reference numerals and in which.

DETAILED DESCRIPTION OF PREFERRED EMBODIMENT(S)

Figure 1:
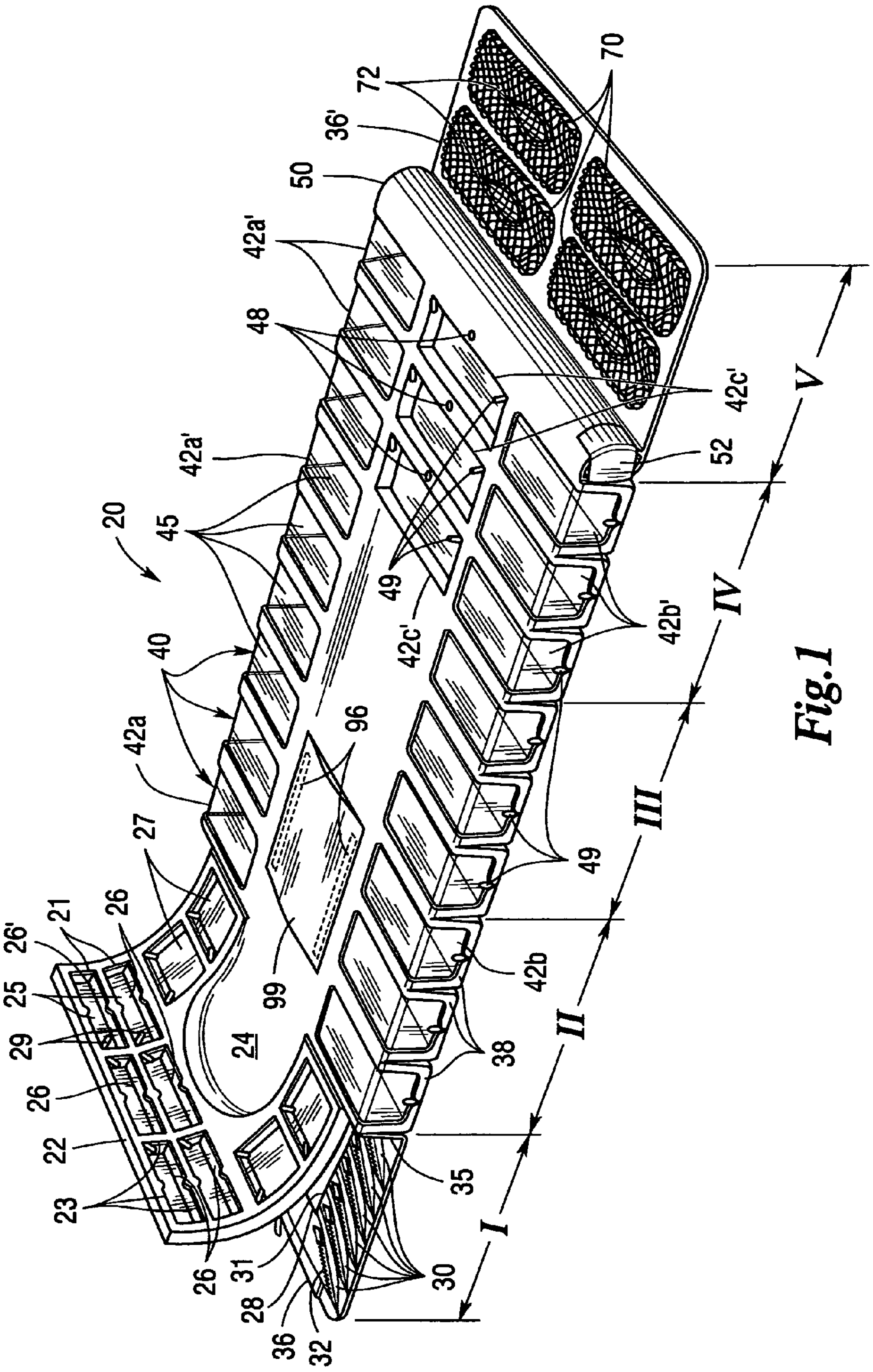
FIG. 1 is a perspective side view of a first embodiment of the portable resuscitation organizer platform of the present invention.

A first preferred embodiment of the portable resuscitation organizer platform (P.R.O.P.) of the present invention is depicted in FIG. 1 generally at 20. In this view, the platform 20 is shown in a deployed, ready-to-use position with the exception that leading end 22 is shown rolled upward to demonstrate its flexibility and reveal equipment stored thereunder.

P.R.O.P. 20 has four basic sections storing anatomically arrayed medical equipment to facilitate the caregiver's access and implementation of the needed materials. Section I comprises the airway station and has a headrest region 24 which is softer and contoured with a scooped out region to better accommodate the patient's head. The equipment stored in this region includes a laryngoscope handle and an assortment of tips (blades) in compartments 26. One of the compartments 26' may contain spare batteries for the laryngoscope.

Figure 2:
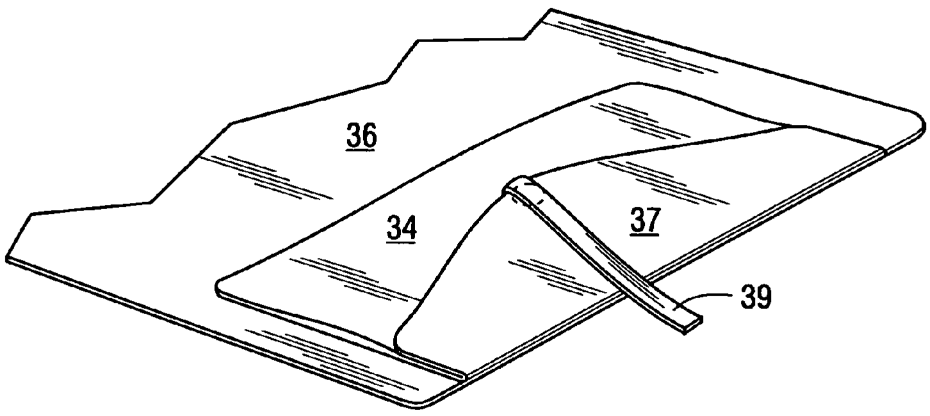
FIG. 2 is a breakaway perspective view of a detail of the first embodiment.

A series of clear plastic envelopes 30 have zippers 32 and are attached to binder 28 along a first edge 31. It will be appreciated that binder 28 is firmly attached to the vertical surface 35 of base 36. Envelopes 30, shown in FIG. 1 as being six in number, extend one half the width of platform 20 with a like number of envelopes positioned on the far side. Envelopes 30 accommodate a variety of sizes of endo-tracheal tubes, stylettes and matching soft suction catheters. Size information may be inserted in the see-through envelope 30 or labels can be applied to an external surface. Other articles for securing the airway including oropharyngeal airways, syringes, and tape or other tube stabilizing device of the caregiver's choice, can be stored in compartments 27. A separate envelope 34 is attached to base 36 and has a pull tab 39 labeled "suction" which protrudes beneath envelopes 30 out the top of platform 20 (FIG. 2). By grasping and pulling on tab 39, flap 37 of envelope 34 can be opened to provide access to a rigid suction wand with suction tubing even when the platform 20 is supporting the patient. All compartments 26, 27 have rugged clear plastic closures 25 with pull tabs 29 which enable their contents to be easily identified and accessed. The closures 25 will preferably be attached to the compartments 26, 27 along one edge 21 and secured along the other three sides 23 by VELCRO hook-and-loop fabric or, as an alternative, a zip-lock style closure.

Figure 3:
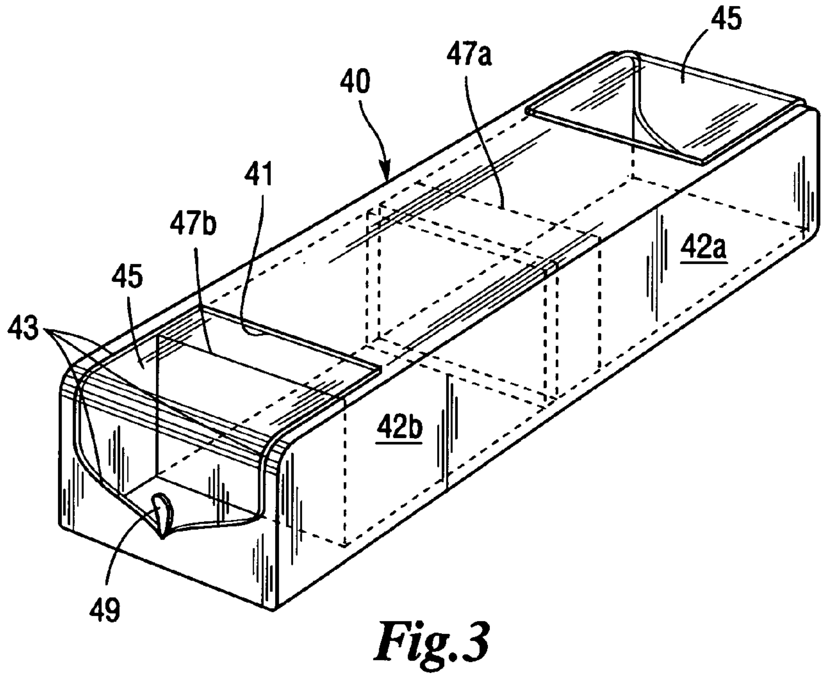
FIG. 3 is a perspective view of a sleeve used in the organizer platform of the first embodiment.

Section II is identified as the "CPR surface". It will support the upper torso of a large child or an adult, or the entire body of a small child or infant, and needs to be rigid so that minimal collapse of the support occurs as heart compressions are administered. Accordingly, the pockets 38 are filled with a plurality of rectangular sleeves 40 made of a rigid, durable plastic, best seen in FIG. 3. In one embodiment, the pockets 38 are constructed of nylon fabric; it is contemplated that in a single use embodiment, less expensive materials may be employed. Each sleeve 40 is divided into two compartments **42*a* and 42*b*; each compartment 42*a*, 42*b* has a closure 45 which, as was the case with closures 25, attached along a first edge 41 and has VELCRO fabric (or a zip-lock fastener) along the other three sides 43 with a pull tab 49 for providing access to the contents of sleeves 40. The sleeves in Section II can contain such items as gloves, EKG electrodes, BP cuffs, stethoscope, and pulse oximeter probes. In order to maintain the items proximate to the opening, each sleeve 40 contains a resilient backing means, such as an expandable foam sponge shown in collapsed condition at 47*a* in the back compartment 42*a* and in the expanded condition at 47*b* in the front compartment 42*b*. It will be understood that resilient backing means 47 will not be appropriate for every compartment 42**, depending on the items contained therein and may be removed for articles (e.g., stethoscope) where their use is not beneficial. Indeed, one of the most attractive features of the P.R.O. platform of the present invention is that the contents can be tailored to fit the preferences of a particular user.

Section III also has sleeves 40 forming ribs extending laterally across the platform and supporting the lower torso of the larger pediatric or adult patient. Section III comprises the bilateral I.V. stations with sleeves 40 containing angio-catheters of various sizes, start kits including prep pads, tourniquets, tape, dressings and related items such as test tubes for blood specimens.

Section IV has pockets with sleeves 40' which provide storage for medication. Sleeves 40' are divided into three compartments **42*a*', 42*b*', 42*c*' with the center compartments 42*c*' providing storage for syringes and the like. The outside compartments 42*a*' and 42*b*' are sized to accommodate the largest boxes of standard emergency medications, such as 50 ml ampules of sodium bicarbonate and 50 ml of 50% dextrose. Other common emergency medications such as epinephrine, atropine and calcium chloride in single dose (10 ml ampules) containers, are sized such that three such containers will fit in compartments 42*a*' and 42*b*'. Obviously, the backing means could be omitted with the 50 ml ampules while they would be used with the 10 ml ampules. Section IV has a plurality of apertures 48 situated between compartments 42*c*'. These apertures will receive an IV support pole 60 described in greater detail below. It is pointed out that these apertures 48** will be situated between the patient's lower limbs so that the IV support pole will be situated out of the way of the care givers working around the patient's head and torso and will not interfere with the patient's comfort.

Figure 7:
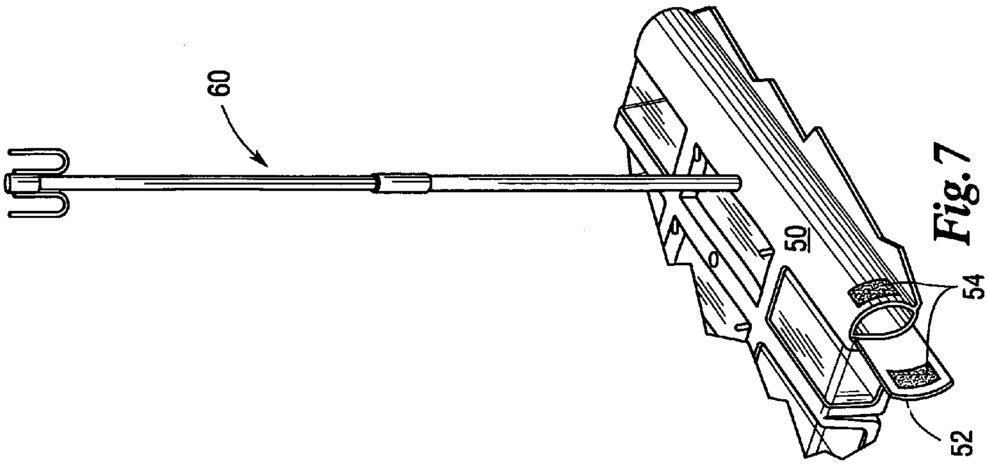
Figure 6:
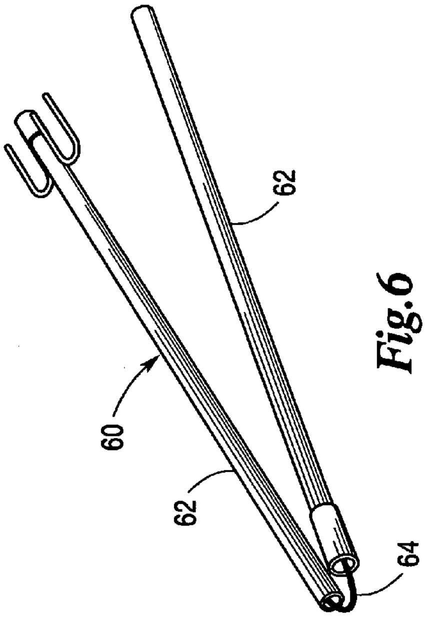
FIG. 6 is a perspective side view of a collapsible IV stand usable with the first embodiment; and, FIG. 7 is a breakaway perspective view showing the IV stand in its assembled configuration.

Section V comprises a secondary base 36' attached to the distal end of Section IV. A full-width enclosure 50 has a securing flap 52 which is attached by VELCRO hook and loop fabric strips 54 (FIG. 7). Within enclosure 50, a collapsible IV support pole 60, as well as other long items such as chest tubes (thoracic catheters), are housed. Support pole 60 is structured like tent poles having rigid sections 62 interconnected by a length of bungee cord 64. In this manner, IV support pole 60 can be collapsed and stored within enclosure 50, yet erected quickly. Section V also has a plurality of mesh bags 70 secured to the upper surface of secondary base 36' with draw strings 72. These mesh bags 70 can secure articles which are too large to fit within the other compartments of the platform 20. Such bulky items might include bag-valve-mask resuscitators (commonly referred to as Ambu-bags) in a variety of sizes for infant, child or adult use. If the patient is a teen or an adult, it would not matter that their legs extended over these bags as the contents of the bags 70 could be easily accessed by momentarily moving the patient's leg.

Figure 5:
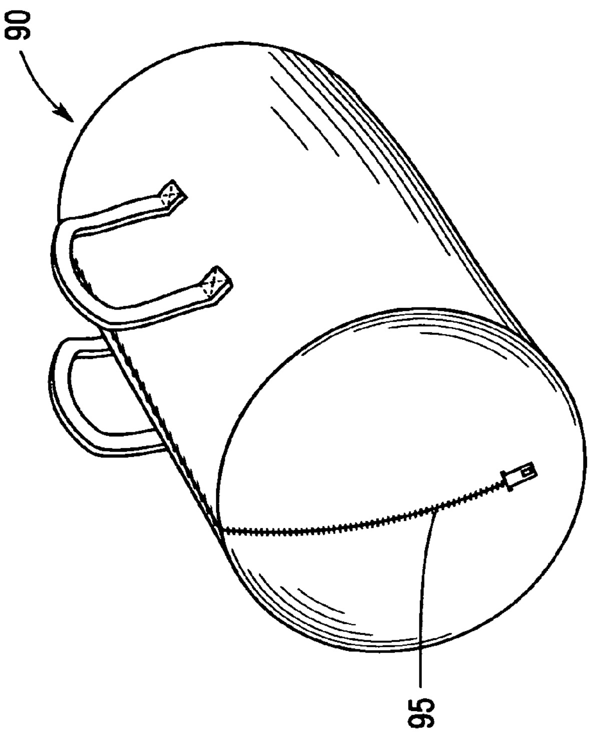
FIG. 5 is a perspective end view of a storage satchel used to retain the first embodiment.
Figure 4:
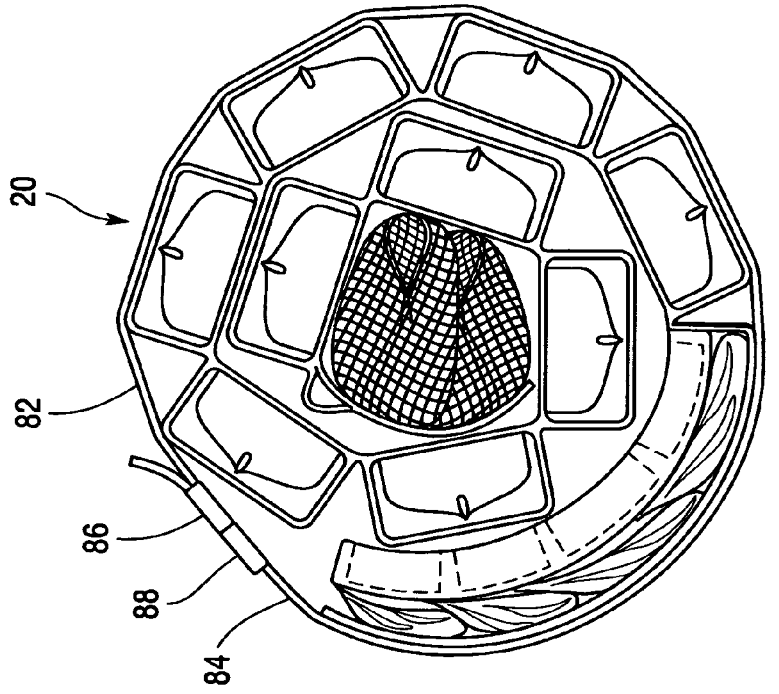
FIG. 4 is a schematic end view of the first embodiment of the organizer platform shown in its storage configuration.

It is envisioned that defibrillation pads which are typically single use, stick-on electrodes could be housed in a separate envelope 99 that would simply be attached to the center region of the P.R.O. platform 20 in below the head rest 24 (FIG. 1) with VELCRO strips 96 prior to rolling the platform up for storage (FIG. 4). In this fashion, the electrodes would be subjected to minimal bending and, therefore, maintain their integrity, while remaining ready for placement on the patient's chest, if needed. Two strap portions 82 and 84 are secured to portions of the exterior of the platform and clip portions 86 and 88 allow the platform to be secured in a bedroll configuration for compact storage. Carrying case 90 (FIG. 5) with zipper 92 can be provided to facilitate storage and transport of platform 20.

The present portable resuscitation organizer platform 20 provides a patient support which can be unrolled on a table, gurney, or, it need be, on the ground. The medical supplies and equipment are anatomically arranged about the patient to provide quick access to treat the particular medical emergency. The see-through closures 45 and transparent envelopes 30, 99 enable identification of the contents with a glance. Backing means 47 is provided in compartments 42 to push the contents to the forefront where they are readily accessible by the care giver. It is anticipated that P.R.O.P.s will be provided in a plurality of sizes, one which accommodates infants and small children and another size for adults. The provision of a medical supply organizer which provides rapid access to the needed items in seconds rather than minutes, can make meaningful difference in the survival and recovery rates of patients.

Various changes, alternatives and modifications will become apparent to one of ordinary skill in the art following a reading of the foregoing specification. For example, it is envisioned that the platform could be simplified for applications where endotracheal needs were not at issue by replacing the airway station of Section I with a pillow. The modified platform could be used for military and civilian medical emergencies enabling any large area, such as a gym, to be converted to a medical response unit to treat victims of terrorism, disasters, or military action. It is intended that any such changes, alternatives and modifications as fall within the scope of the appended claims be considered part of the present invention.

I claim:

1. A portable organizer platform for use in performing emergency medical care on a patient comprising
- a) a plurality of interconnected support members for underlying the patient, each of said plurality of interconnected support members being formed as a sleeve for receiving a plurality of articles, each sleeve having closure means on at least one end, said closure means being transparent to display the articles within, wherein at least some of said sleeves are rigid in order to support the weight of the patient without collapsing, said sleeves forming said rigid support means;
- b) compartments and envelopes associated with said support members, said compartments and envelopes being anatomically arranged around the patient in regions adjacent body portions where items contained in said compartments and envelopes will be needed for treatment of the patient, the items comprising airway opening apparatus including a laryngoscope and endotracheal tubes positioned around a head rest region for the patient;
- c) said plurality of interconnected support members forming a rigid support surface positioned to lie beneath a chest portion of the patient to permit CPR to be administered;
- d) means for retaining said portable organizer platform in a collapsed condition for facilitating transport.

2. The portable organizer platform of claim 1 wherein said rigid sleeves have a resilient backing means in an inner portion thereof to push items contained therein toward one end thereof to facilitate their acquisition.

3. The portable organizer platform of claim 1 wherein at least some of said plurality of sleeves are rectangular in cross section.

4. The portable organizer platform of claim 3 further comprising a plurality of envelopes positioned in an overlapping array adjacent a head/shoulder region of the patient.

5. The portable organizer platform of claim 4 further comprising a plurality of netting bags equipped with drawstrings for housing bulky items.

6. The portable organizer platform of claim 1 wherein said means for retaining comprises an adjustable strap for securing said organizer platform in a bed-roll configuration.

7. The portable organizer platform of claim 6 wherein said means for retaining further comprises a duffle-bag-style carrying case for receiving said portable organizer platform.

8. The portable organizer platform of claim 1 wherein said head rest region is formed of softer material to accommodate a head of the patient.

9. The portable organizer platform of claim 8 wherein said head rest region is contoured with a scooped out area to better accommodate the patient's head.

10. The portable organizer platform of claim 1 further comprising an IV support stand collapsible to a size capable of being received within one of said compartments.

11. The portable organizer platform of claim 10 further comprising a receptacle formed in said support members for receiving said IV stand.

12. The portable organizer platform of claim 1 further comprising a separable envelope for securing single use, stick-on electrodes employed as defibrillation pads having means for securing said envelope within a portion of said organizer platform in a chest-area of the patient.

13. The portable organizer platform of claim 1 wherein the anatomically arranged items further comprise I.V. equipment within said rigid sleeves including angiocatheters of various sizes, start kits including prep pads, tourniquets, tape, dressings and related items such as test tubes for blood specimens positioned along each side of the patient.

14. The portable organizer platform of claim 1 further comprising three sets of compartments positioned across an end of said organizer platform distal from said head rest region, said three sets of compartments being adapted to store medications.

15. The portable organizer platform of claim 1 further comprising a plurality of expandable mesh bags capable of receiving items too large to fit within any remaining compartment of said organizer platform.

16. A portable organizer platform for use in performing emergency medical care on a patient comprising
- a) a plurality of interconnected support members for underlying the patient each of said plurality of interconnected support members being formed as a sleeve for receiving a plurality of articles, at least some of said plurality of sleeves being rectangular in cross section;
- b) compartments associated with said support members;
- c) a plurality of envelopes positioned in an overlapping array adjacent a head/shoulder region of the patient, said compartments and envelopes being anatomically arranged around the patient in regions adjacent body portions where items contained in said compartments and envelopes will be needed for treatment of the patient, the items including airway opening apparatus including a laryngoscope and endo-tracheal tubes positioned around a head rest region for the patient
- d) a rigid support platform positioned to lie beneath a chest portion of the patient to permit CPR to be administered;
- e) means for retaining said portable organizer platform in a collapsed condition for facilitating transport.

17. The portable organizer platform of claim 16 wherein at least some of said plurality of sleeves are rigid in order to support the weight of the patient without collapsing, said sleeves forming said rigid support means.

18. The portable organizer platform of claim 16 further comprising a resilient backing means in an inner portion of said sleeves to push items contained therein toward one end thereof to facilitate their acquisition.

19. The portable organizer platform of claim 16 further comprising closure means for at least one end of each of said sleeves.

20. The portable organizer platform of claim 19 wherein said closure means is transparent enabling an attendant to readily identify the contents of a particular one of said sleeves.

* * * * *